(12) United States Patent
Schuren et al.

(10) Patent No.: US 8,058,468 B2
(45) Date of Patent: Nov. 15, 2011

(54) CARBAMATE ANTIBIOTICS

(75) Inventors: Frank Henri Johan Schuren, Veenendaal (NL); Henricus Matheus Wilhelmus Maria Thijssen, Houten (NL); Roy Christiaan Montijn, Amsterdam (NL)

(73) Assignee: Nederlandse Organisatie Voor Toegepast-Natuurwetenschappelijk Onderzoek TNO, Delft (NL)

( * ) Notice: Subject to any disclaimer, the term of this patent is extended or adjusted under 35 U.S.C. 154(b) by 529 days.

(21) Appl. No.: 12/097,843

(22) PCT Filed: Dec. 21, 2006

(86) PCT No.: PCT/NL2006/000651
§ 371 (c)(1),
(2), (4) Date: Dec. 17, 2008

(87) PCT Pub. No.: WO2007/073168
PCT Pub. Date: Jun. 28, 2007

(65) Prior Publication Data
US 2009/0192221 A1    Jul. 30, 2009

(30) Foreign Application Priority Data
Dec. 21, 2005   (EP) .................................. 05077956

(51) Int. Cl.
*C07C 271/02* (2006.01)
*C07C 271/06* (2006.01)
*A61P 31/04* (2006.01)

(52) U.S. Cl. ................ 560/25; 560/24; 560/30; 560/31; 560/32; 560/33

(58) Field of Classification Search ........................ None
See application file for complete search history.

(56) References Cited

FOREIGN PATENT DOCUMENTS
EP      1 142 868       10/2001

OTHER PUBLICATIONS

Orzeszko et al. Journal of Applied Polymer Science, 1980, 25, 2969-2973.*
Chemical Abstracts Service, Columbus, Ohio, US, XP002385818.

* cited by examiner

*Primary Examiner* — Daniel Sullivan
*Assistant Examiner* — Yevegeny Valenrod
(74) *Attorney, Agent, or Firm* — Lucas & Mercanti, LLP

(57) ABSTRACT

The invention relates to the field of antibiotic compositions, both inside and outside the medical field. Presented is a new class of antibiotic compounds around the lead compound (3,4-dichloro-phenyl)-carbamic acid 2-isobutoxycarbonylamino-1-methyl-ethyl ester, which are especially useful for combating infections with gram-positive bacteria and especially MRSA.

8 Claims, 2 Drawing Sheets

CARBAMATE ANTIBIOTICS

The invention relates to the field of pharmaceutical compounds, especially antibiotic compounds.

Searching for novel antibiotic compounds has become more and more important, especially since many micro-organisms are becoming resistant to known antibiotic compounds. This is especially the case for a group of *Staphylococcus aureus* bacteria, which are now identified as MRSA (methicillin-resistant *S. aureus*). Therefore, there is an ever increasing need for new antibiotic compounds, which can be used against micro-organisms that have become resistant to commonly used antibiotics.

The present inventors have developed a new test and detection system to search for novel antibiotics and novel targets for antibiotics. This system is the subject of several copending applications (WO 03/0087397, WO 03/0981389, WO 05/0035782, WO 05/106033). Using this system now a new class of antibiotics has been uncovered.

The presently disclosed new class of antibiotics covers compounds with the general formula (I):

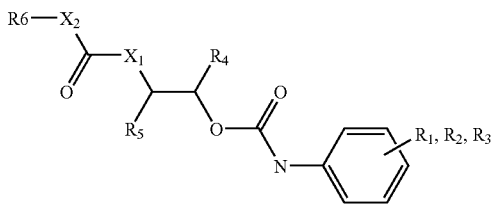

wherein $R_1$, $R_2$, $R_3$ are each independently hydrogen, halogen, loweralkyl, loweralkoxy, substituted loweralkyl or loweralkoxy, $R_4$ and $R_5$ are each independently hydrogen or loweralkyl, $R_6$ is hydrogen, loweralkyl, loweralkoxy, aryl, substituted loweralkyl, loweralkoxy or aryl, $X_1$ is N or O, $X_2$ is C, N or O, with the proviso that $X_1$ and $X_2$ can not be both N or both O.

DETAILED DESCRIPTION OF THE INVENTION

Figure 1:
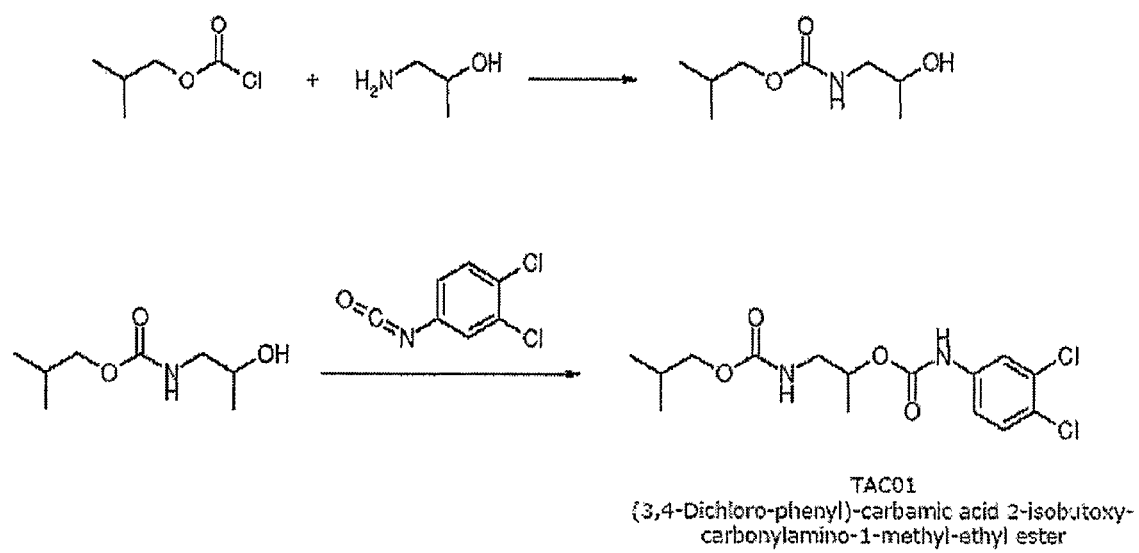
FIG. 1 shows the synthetic route for (3,4-dichloro-phenyl)-carbamic acid 2-isobutoxycarbonylamino-1-methyl ethyl ester.

The term "alkyl" or "lower alkyl" refers to an alkyl radical containing one to six carbon atoms including, but not limited to, methyl, ethyl, propyl, isopropyl, n-butyl, t-butyl and neopentyl. The alkyl chain can be straight or branched.

The term "loweralkoxy" refers to a loweralkyl group as previously defined attached to a parent molecular moiety by an ether linkage.

The term "loweralkoxy (methyl)" refers to an alkoxy group as described above attached to a parent molecular moiety via a methylene group (—CH$_2$—).

The term "aryl" as used herein refers to a mono-or bicyclic carbocyclic ring system having one or two aromatic rings including, but not limited to, phenyl, naphthyl, tetrahydronaphthyl, indanyl, indenyl and the like. Aryl groups (including bicyclic aryl groups) can be unsubstituted or substituted with one, two or three substituents independently selected from loweralkyl, substituted loweralkyl, haloalkyl, alkoxy, thioalkoxy, amino, alkylamino, dialkylamino, acylamino, benzyloxycarbonyl, cyano, hydroxyl, halo, mercapto, nitro, carboxaldehyde, carboxy, alkoxycarbonyl, carboxamide, and protected hydroxyl. In addition, substituted aryl groups include tetrafluorophenyl and pentafluorophenyl.

The term "heteroaryl", as used herein, refers to a mono-or bicyclic fused aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "substituted alkyl or alkoxy" as used herein refers to an alkyl or alkoxy group as defined herein substituted by independent replacement of one, two or three of the hydrogen atoms thereon with Cl, Br, F, I, OH, CN, haloalkyl, thioalkoxy, amino, alkylamino, dialkylamino, mercapto, nitro, carboxaldehyde, carboxy, alkoxycarbonyl and carboxamide.

The term "substituted aryl" as used herein refers to an aryl group as defined herein substituted by independent replacement of one, two or three of the hydrogen atoms thereon with Cl, Br, F, I, OH, CN, $C_1$-$C_3$-alkyl, $C_1$-$C_6$-alkoxy, $C_1$-$C_6$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group. Also, substituted aryl groups include tetrafluorophenyl and pentafluorophenyl.

The term "substituted heteroaryl" as used herein refers to a heteroaryl group as defined herein substituted by independent replacement of one, two or three of the hydrogen atoms thereon with Cl, Br, F, I, OH, CN, $C_1$-$C_3$-alkyl, $C_1$-$C_6$-alkoxy, $C_1$-$C_6$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group.

The term "pharmaceutically acceptable salts" as used herein refers to those carboxylate salts, esters, and prodrugs of the compound of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

Pharmaceutically acceptable salts are well known in the art and refer to the relatively non-toxic, inorganic and organic acid addition salts of the compounds of the present invention. For example, S. M. Berge, et al. describe pharmaceutically acceptable salts in detail in J. Pharmaceutical Sciences, 66: 1-19 (1977) which is incorporated herein by reference. The salts can be prepared in situ during the final isolation and purification of the compounds of the invention, or separately by reacting the free base function with a suitable organic acid.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, stearate, succinate, sulphate, tartrate, thiocyanate, p-toluenesulphonate, undecanoate, valerate salts, and the like. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulphate, phosphate, nitrate, lower-alkyl sulphonate and aryl sulphonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable solvate" represents an aggregate that comprises one or more molecules of the solute, such as a compound of the invention, with one or more molecules of solvent.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A. C. S. Symposium Series, and in Edward B. Roche, ed., Bioreversible Carriers in Drug Design, American Pharmaceutical Association and Pergamon Press, 1987, both of which are incorporated herein by reference.

Preferred compounds according to formula (I) are those compounds in which both $R_1$ and $R_2$ are Cl, while $R_3$ is H. Also preferred are compounds according to formula (I) wherein $X_1$ is N and $X_2$ is O. Most preferred is a compound, wherein $R_1=R_2=Cl$, and located at the para- and meta-position on the phenyl-ring, $R_3=H$, $R_4=H$ or $CH_3$, $R_5=H$, $CH_3$ or $CH_2CH_3$, $X_1=N$, $X_2=O$, R6 is $CH_3$, $CH_2CH_3$, $CH(CH_3)_2$ or $CH_2CH(CH_3)_2$.

The compounds (3,4-dichloro-phenyl)-carbamic acid 2-ethoxycarbonylamino-ethyl ester (CAS Nr. 306316-43-8; BAS 00212008), (3,4-dichloro-phenyl)-carbamic acid 2-isopropoxycarbonylamino-butyl ester (CAS Nr. 331959-00-3; BAS 00674544) and (3,4-dichloro-phenyl)-carbamic acid 2-isobutoxycarbonylamino-1-methyl ethyl ester (CAS Nr. 331959-03-6; BAS 00674552) are commercially available from Asinex (Moscow, Russia), TimTec (Newark, USA) and Interchim (Montlucon, France), respectively.

A possible synthetic route for (3,4-dichloro-phenyl)-carbamic acid 2-isobutoxycarbonylamino-1-methyl ethyl ester is depicted in FIG. 1. It follows from this scheme that the herein mentioned compounds of the invention according to formula (I) can be prepared in a similar way by changing the starting or reactant components. These changes will be apparent to a person skilled in the art.

The compounds according to formula (I) have antibiotic activity, in particular against Gram positive bacteria. They are especially active against staphylococcal and enterococcal strains, and in particular against *S. aureus*, including also the strains of *S. aureus*, that are commonly known as MRSA strains.

They can be used in pharmaceutical compositions for the treatment of bacterial diseases, especially those diseases caused by the above mentioned micro-organisms, or in conditions wherein the subject runs the risk of being infected with micro-organisms.

The compounds of the invention or compositions therewith can, however, also be used in other than pharmaceutical applications, e.g. in cosmetics (e.g. for the treatment of acne), in detergents and/or other cleaning solutions, in anti-fouling paints, in food or feed or in food or feed packaging, and so on.

A compound according to the formula (I), or a pharmaceutically acceptable salt or prodrug thereof, may be provided to a subject in need thereof for prophylactic or therapeutic reasons. A compound according to the formula (I), or a pharmaceutically acceptable salt or prodrug thereof, may be provided to a subject in need thereof in the form of any pharmaceutical preparation, when such administration form is capable of treating and/or preventing infection in a subject. As a consequence of the prevention or treatment of infection, also the clinical effects or sequellae of infection will be prevented.

The present invention also relates to a method for preventing and/or treating infection in a subject, preferably a human or other mammalian subject, said method comprising administering to said subject a therapeutically and/or prophylactically effective amount of a pharmaceutical composition comprising a compound according to formula (I), more preferably a compound as depicted in Table 1, or pharmaceutically acceptable salts or prodrugs thereof and a pharmaceutically acceptable carrier, and optionally one or more excipients.

The present invention also relates to the use of a compound according to formula (I), more preferably a compound as depicted in Table 1 or pharmaceutically acceptable salts or prodrugs thereof for the manufacture of a medicament for treating infection, preferably bacterial infections, most preferably staphylococcal or enterococcal infection.

An antibiotic therapy (i.e. the method for preventing and/or treating infection in a subject) may also comprise administering to an otherwise healthy individual, at risk of developing infection, a prophylactically effective amount of the pharmaceutical composition.

Dosages for achieving the antibiotic effects of the pharmaceutical composition described herein may easily be determined by the skilled person. For purposes of the present invention, an effective dose will be a daily dose between about 0.01 mg and 10 grams of the compound according to formula (I) for an adult human being. More preferably a dose between 0.1 mg and 1 gram is used, even more preferably a dose of 1 mg-100 mg and most preferably a dose of 4-40 mg of the compound of the invention is administered. This daily dose may be given as a one-dose administration, or it may be subdivided in several subdoses, which are administered spread over the day.

For oral administration, the compositions may be packed in e.g. gelatin capsules or may be tabletted in the form of tablets. For oral therapeutic application the active compound may be administered with excipients and e.g. used in the form of powders, sachets, tablets, pills, pastilles or capsules. The pharmaceutical compositions may be prepared by conventional means with pharmaceutically acceptable excipients such as binding agents (e.g. pregelatinised maize starch, tragacanth gum, gelatin, polyvinylpyrrolidone or hydroxypropyl methylcellulose); fillers (e.g. lactose, microcrystalline cellulose, mannitol or calcium hydrogen phosphate); lubricants (e.g. magnesium stearate, talc or silica); disintegrants (e.g. potato starch, sodium starch glycollate or alginate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration the compositions may take the form of tablets or lozenges formulated in conventional manner.

The compounds according to the present invention may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g. sterile pyrogen-free water, before use.

When dosing is in the form of a capsule, the capsule may comprise apart from the elements mentioned above a liquid carrier such as an oil. Dosage form may further be provided with coatings of sugar, shellac or other agents. The components of the pharmaceutical composition are preferably chosen such that they do not reduce the desired working of the active compound.

The pharmaceutical compositions can further comprise flavoring sweetening, coloring and/or preservative agents.

A compound according to the formula (I), or a pharmaceutically acceptable salt or prodrug thereof may also be administered in the form of e.g. an elixir, a suspension, a syrup, a waffle or a chewing gum.

In a pharmaceutical composition as described above, a compound according to the formula (I), or a pharmaceutically acceptable salt or prodrug thereof, is used in an amount of from 0.01 to 99.9% by weight, preferably from 0.01 to 10 wt. %, and more preferably from 0.05 to 5 wt. %.

The present invention further relates to a method for the preparation of a pharmaceutical composition for preventing and/or treating infection, comprising processing or incorporating a compound according to the formula (I), or a pharmaceutically acceptable salt or prodrug thereof, as an active substance, together with a pharmaceutically acceptable carrier in a pharmaceutical composition.

The preparation of a pharmaceutical composition may very suitably occur by mixing all separate ingredients such as fillers, binders, lubricants and optionally other excipients together with a compound according to the formula (I), or a pharmaceutically acceptable salt or prodrug thereof, and processing the mixture obtained to a pharmaceutical preparation.

TABLE I

Exemplary compounds of general formula I. For $R_1$, $R_2$, and $R_3$ is indicated whether the indicated moieties are in the para (p-), meta (m-) or ortho (o-) position

| Compound | $R_1$ | $R_2$ | $R_3$ | $R_4$ | $R_5$ | $X_1$ | $X_2$ | $R_6$ |
|---|---|---|---|---|---|---|---|---|
| BAS00212008 (NewCo001) | p-Cl | m-Cl | H | H | H | N | O | ethyl |
| BAS00674544 (NewCo002) | p-Cl | m-Cl | H | H | ethyl | N | O | isopropyl |
| BAS00674552 (NewCo003) | p-Cl | m-Cl | H | $CH_3$ | H | N | O | isobutyl |
| NewCo004 (=TAC1_009) | p-Cl | m-Cl | H | H | H | O | N | H |
| NewCo005 (=TAC1_011) | p-Cl | m-Cl | H | H | H | O | N | ethyl |
| NewCo006 | p-Cl | m-Cl | H | H | H | O | N | $SO_2$-methyl |
| NewCo007 | p-Cl | m-Cl | H | H | H | N | C | H |
| NewCo008 (=TAC1_010) | p-Cl | m-Cl | H | H | H | O | N | $CH_3$ |
| NewCo009 (=TAC1_012) | p-Cl | m-Cl | H | H | H | O | N | isobutyl |
| NewCo0010 | p-Cl | m-Cl | H | H | H | O | N | $SO_3$ |
| NewCo0011 | p-Cl | m-Cl | H | H | H | N | C | O—$CH_3$ |
| NewCo0020 (=TAC1_015) | p-Cl | m-Cl | H | H | H | N | O | $CH_3$ |
| NewCo0012 (=TAC1_016) | p-$CH_3$ | m-$CH_3$ | H | $CH_3$ | H | N | O | isobutyl |
| NewCo0013 (=TAC1_003) | p-O—$CH_3$ | m-O—$CH_3$ | H | $CH_3$ | H | N | O | isobutyl |

TABLE I-continued

Exemplary compounds of general formula I. For $R_1$, $R_2$, and $R_3$ is indicated whether the indicated moieties are in the para (p-), meta (m-) or ortho (o-) position

| Compound | $R_1$ | $R_2$ | $R_3$ | $R_4$ | $R_5$ | $X_1$ | $X_2$ | $R_6$ |
|---|---|---|---|---|---|---|---|---|
| NewCo0014 (=TAC1__005) | p-CH$_3$ | H | H | CH$_3$ | H | N | O | isobutyl |
| NewCo0015 (=TAC1__007) | p-CF$_3$ | H | H | CH$_3$ | H | N | O | isobutyl |
| NewCo0016 (=TAC1__002) | p-F | m-F | H | CH$_3$ | H | N | O | isobutyl |
| NewCo0017 | p-CF$_3$ | m-CF$_3$ | H | CH$_3$ | H | N | O | isobutyl |
| NewCo0018 (=TAC1__006) | p-O—CH$_3$ | H | H | CH$_3$ | H | N | O | isobutyl |
| NewCo0019 (=TAC1__008) | H | m-CF$_3$ | H | CH$_3$ | H | N | O | isobutyl |

The chemical names of these compounds are provided in the following list:

NewCo001: (3,4-dichloro-phenyl)-carbamic acid 2-ethoxycarbonylamino-ethyl ester (CAS-Nr. 306316-43-8)

NewCo002: (3,4-dichloro-phenyl)-carbamic acid 2-isopropoxycarbonylamino-butyl ester (CAS-Nr. 331959-00-3)

NewCo003: (3,4-dichloro-phenyl)-carbamic acid 2-isobutoxycarbonylamino-1-methyl-ethyl ester (CAS-Nr. 331959-03-6)

NewCo004: (3,4-dichloro-phenyl)-carbamic acid 2-carbamoyloxy-ethyl ester

NewCo005: (3,4-dichloro-phenyl)-carbamic acid 2-ethylcarbamoyloxy-ethyl ester

NewCo006: (3,4-dichloro-phenyl)-carbamic acid 2-methanesulfonylcarbamoyloxy-ethyl ester NewCo007: (3,4-dichloro-phenyl)-carbamic acid 2-acetylamino-ethyl ester NewCo008: (3,4-dichloro-phenyl)-carbamic acid 2-methylcarbamoyloxy-ethyl ester NewCo009: (3,4-dichloro-phenyl)-carbamic acid 2-isopropylcarbamoyloxy-ethyl ester NewCo0010: (3,4-dichloro-phenyl)-carbamic acid 2-(sulfonic acid)carbamoyloxy-ethyl ester NewCo0011: (3,4-dichloro-phenyl)-carbamic acid 2(2-methoxy-acetylamino)-ethyl ester NewCo0012: (3,4-dichloro-phenyl)-carbamic acid 2-isobutoxycarbonylamino-1-methyl-ethyl ester NewCo0013: (3,4-dimethoxy-phenyl)-carbamic acid 2-isobutoxycarbonylamino-1-methyl-ethyl ester NewCo0014: p-tolyl-carbamic acid 2-isobutoxycarbonylamino-1-methyl-ethyl ester NewCo0015: (4-trifluoromethyl-phenyl)-carbamic acid 2-isobutoxycarbonylamino-1-methyl-ethyl ester NewCo0016: (3,4-difluoro-phenyl)-carbamic acid 2-isobutoxycarbonylamino-1-methyl-ethyl ester NewCo0017: (3,4-bis-trifluoromethyl-phenyl)-carbamic acid 2-isobutoxycarbonylamino-1-methyl-ethyl ester NewCo0018: (4-methoxy-phenyl)-carbamic acid 2-isobutoxycarbonylamino-1-methyl-ethyl ester NewCo0019: (3-trifluoromethyl-phenyl)-carbamic acid 2-isobutoxycarbonylamino-1-methyl-ethyl ester

EXAMPLES

Example 1

MIC Tests

MIC test were performed according to standard methodology: M7-A6-"Methods for Dilution Antimicrobial Susceptibility Tests for Bacteria That Grow Aerobically"; *Approved Standard*, Sixth Edition Clinical and Laboratory Standards Institute 2005 (CLSI/formerly NCCLS).

Table 2 lists the results of 3 different compounds according to Formula (I) on single strains of *S. aureus* as MIC values expressed in micrograms per milliliter.

Table 3 lists the results of experiments on multiple strains of *S. aureus*. The MIC values are expressed as a range between the lowest value and the highest value found in these experiments. Both the average MIC50 and MIC90 are indicated in bold. Again BAS 00674552 is found to be the most active.

TABLE 2

| | | MIC DETERMINATION SINGLE STRAINS | | |
|---|---|---|---|---|
| ID Number | CAS | *S. aureus* ATCC 29213 | *S. aureus* MW2 | *S. aureus* N315 |
| BAS 00674552 | 331959-03-6 | 8 | 4 | 4 |
| BAS 00674544 | 331959-00-3 | 8 | 8 | 8 |
| BAS 00212008 | 306316-43-8 | 16 | 16 | 8 |

TABLE 3

| Compound | No of tested *S. aureus* strains. | Range MIC (lowest-highest) (microgram/milliliter) | | MIC 50 | MIC 90 |
|---|---|---|---|---|---|
| BAS 00674552 | 60 | 4 | >32 | 8 | 16 |
| BAS 00674544 | 60 | 8 | >32 | 16 | 32 |
| BAS 00212008 | 59 | >32 | >32 | >32 | >32 |

Example 2

The purpose of this study was to investigate the antibiotic efficacy of different doses of compound BAS00674552 against a local infection with MRSA 2141 in the mouse. Thirty mice were treated intravenously with 0.5, 5.0 or 50 mg/kg body weight, respectively. The observation period was three days. Outgrowth of the infection was used to establish drug efficacy.

Test substance name: BAS00674552 (in vivo)

For each administered dose, the sponsor provided the appropriate stock solutions as 1 ml aliquots of the test substance in the vehicle (DMSO). These stock solutions were stored at 2-8° C. for 16 hours.

Positive control: Vancomycin (Vancomycine 500 PCH, vancomycinehydrochloride voor i.v. gebruik, chargenr. 03L19A, expiry date: NOV-2005, Pharmachemie, Haarlem, The Netherlands)

Animals and Housing Conditions

| | |
|---|---|
| Species: | mouse |
| Strain: | Swiss out bred (IcoCaw OF1) |
| Supplier: | Charles River Nederland, The Netherlands |
| Sex and age: | 50 female, 6-8 weeks old upon arrival |
| Identification: | the animals were individually marked on the tail |
| Acclimatization period: | 7 days |
| Caging: | 5 animals/sex per cage (Macrolon cages with filter top, and environmental enrichment: shreds of paper. |
| Handling: | mice were handled under laminar flow |
| Lighting: | 12 hour light/12 hour dark cycle |
| Temperature during testing: | 22 ± 3° C. |
| Humidity during testing: | 30%-70% |
| Ventilation: | ca 10 air changes/hour |
| Diet: | ad libitum; SDS D3 food (Special Diets Service, Witham, England) certificate of analysis on request. Tap water, suitable for human consumption (Hydron Midden Nederland). |

Administration of the Test Substance

The test substances were administered as a solution in dimethylsulfoxide (DMSO). The test substance was administered as 20 µl injections per mouse at all dose levels. Vancomycin was used as positive control and injected intravenously as a 10 mg/ml solution in DMSO (20 µl per mouse).

Fresh dilutions of the test substance in vehicle were provided by the sponsor, stored at 2-8° C., and used within 18 hours after preparation. Shortly before injection the test substance were warmed to room temperature.

Study Design and Dose Levels

The study was performed according to Lab-Sop-Amp-Anim-002 and Lab-Sop-Amp-Bac-003. In short, mice were injected with 11E05 MRSA bacteria, strain 2141 in the right thigh muscle, followed one day later by an i.v. injection of the test compound, vancomycin or vehicle in the tail vein. 24 hours later mice were sacrificed, blood was collected by heart puncture and the right thigh muscle was removed. Plasma was prepared from blood samples and stored at −80°±10° C. for possible future analysis. Thigh muscles were weighted and homogenized using an Ultra-Turrax® and dilutions of the homogenate were prepared in saline. Limiting dilutions were plated onto agar plates and two days later the number of MRSA 2141 CFU were determined for each individual mouse as an indication of bactericidal activity of the compound. Additionally, tests were performed to determine if the bacteria used are still oxacillin resistant *Staphylococcus aureus*. This was done before injection and on pooled thigh muscle isolates per group. For this purpose Staphaurex® (Remel Europe Ltd., Crossways, UK) and ORSAB®+supplements (Oxoid Ltd., Basingstoke, UK) were used. In vivo antibiotic activity is determined by a CFU reduction of >90% (1 log reduction) in comparison to the negative control (vehicle only).

Dose Levels

The study was comprised five groups of 10 females each.

The groups are presented in Table 4 below:

TABLE 4

| Group | Color code | Dose levels (mg/kg body weight)[1] | Concentration (mg/ml) | Dose volume (ml/kg) | Number of mice (♀) |
|---|---|---|---|---|---|
| A 0[1] | White | 0 | 0 | 1 | 10 |
| B 0.05 | Green | 0.5 | 0.5 | 1 | 10 |
| C 0.5 | Blue | 5 | 5 | 1 | 10 |
| D 5 | Red | 50 | 50 | 1 | 10 |
| E vanco | Brown | 10 | 10 | 1 | 10 |

[1]vehicle only (DMSO)

In Vivo Effect of Single Dose of Compound BAS00674552

Figure 2:
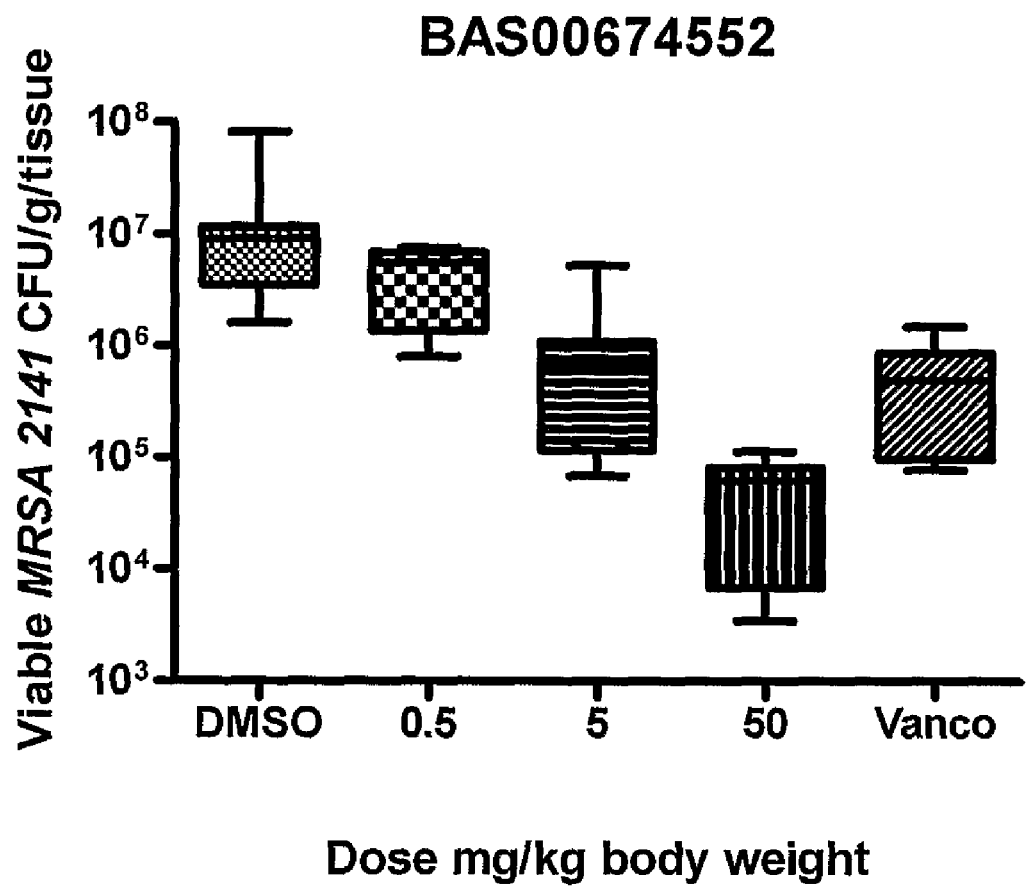
FIG. 2 shows dosis-effect results of various doses of (3,4-dichloro-phenyl)-carbamic acid 2-isobutoxycarbonylamino-1-methyl ethyl ester in mice against *Staphylococcus aureus*.

The results of the vivo data from the experiment are presented graphically (FIG. 2) and show:

1. Bacterial outgrowth in mice that received vehicle (DMSO) only
2. Over 1 Log reduction in the population treated with vancomycin (positive control)
3. Approximately 2 Log reduction in the groups (5 and 50 mg/kg) treated with the test substances.

A statistical analysis (using GraphPad Prism (V3) of the experimental data shows that the compound BAS00674552 was effective ($P \leq 0.001$) against a local MRSA 2141 infection. Individual analysis of the compound at different doses against the untreated group indicate that significant reduction of bacterial outgrowth was achieved by the compound at 5 mg/kg ($P \leq 0.01$) and 50 mg/kg ($P \leq 0.01$) doses, and a significant trend of dose-dependent efficacy was observed.

All animals scored below the value of eight (8) (according Guidelines Dutch local Committee for Animal Experiments (DEC)) on the observation scoring sheets, no signs of adverse side effects were observed.

Example 3

Synthesis of BAS00674552 Analogs (Bicarbamates)

Synthesis of the desired carbamates according to Synthetic scheme 1 proceeded smoothly when heated to reflux in toluene overnight. After cooling some of the end product TAC1_13 002 (58 mg), TAC1__003 (63 mg) and TAC1__007 (111 mg) crystallized from the solution in good purity. End products TAC1__016 (37 mg), TAC1__006 (35 mg) and TAC1__008 (26 mg) were purified by preparative LCMS, yields are shown in the scheme below. Unfortunately end product TAC1__005 was not pure enough after preparative LCMS. Resynthesis was set in and after purification by flash chromatography product TAC1__005 is pure according to LCMS analysis. Resynthesis of TAC1__005 yielded eventually 25 mg of compound.

Synthetic Scheme 1
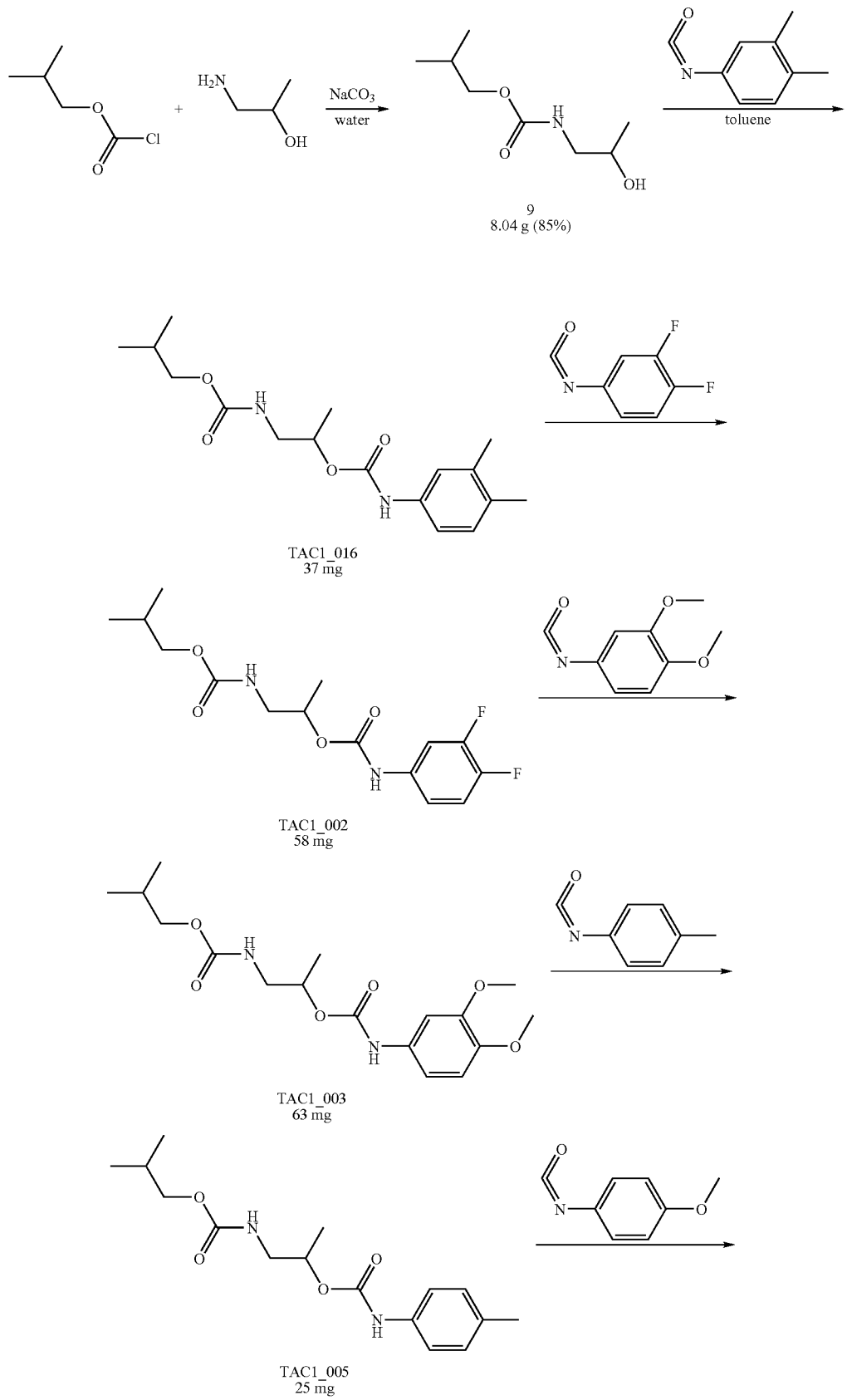

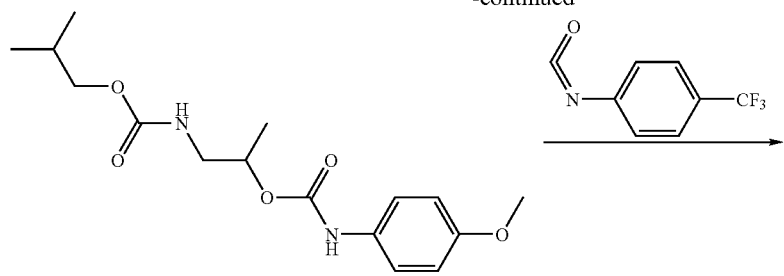
TAC1_006
35 mg
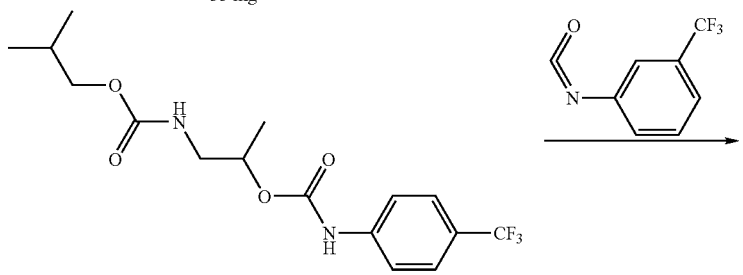
TAC1_007
111 mg
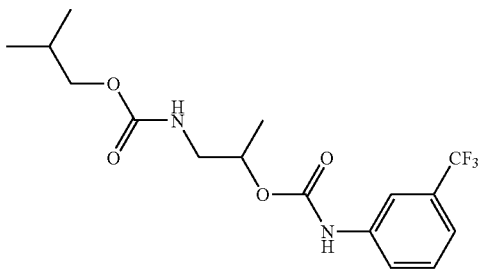
TAC1_008
26 mg
Synthetic scheme 2
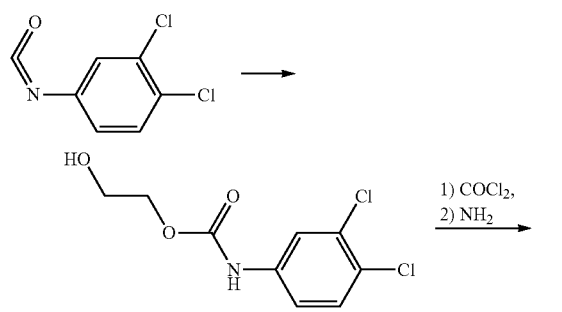
TAC1_009
ME20050189-9
10-20 mg
>95%
-continued
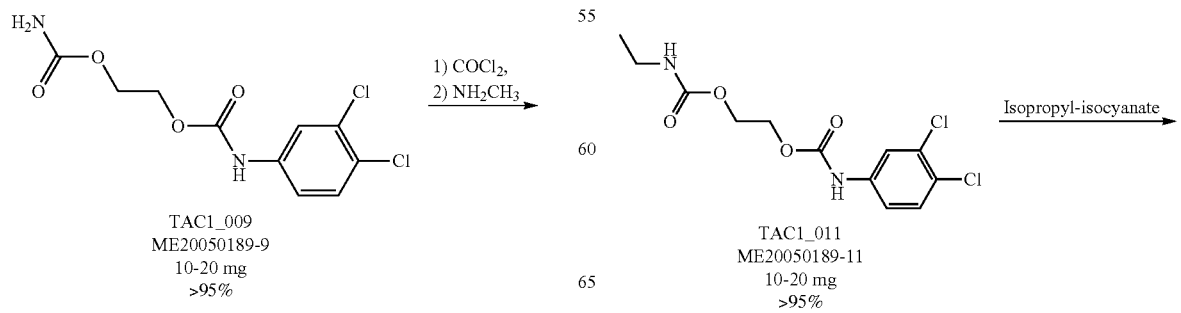
TAC1_010
ME20050189-10
10-20 mg
>95%
TAC1_011
ME20050189-11
10-20 mg
>95%

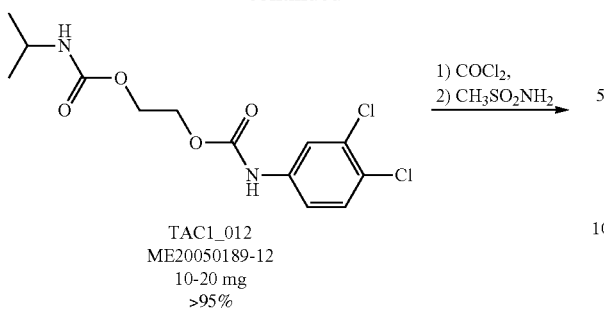
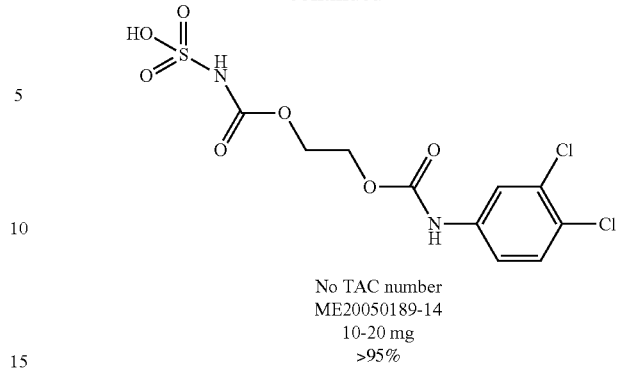
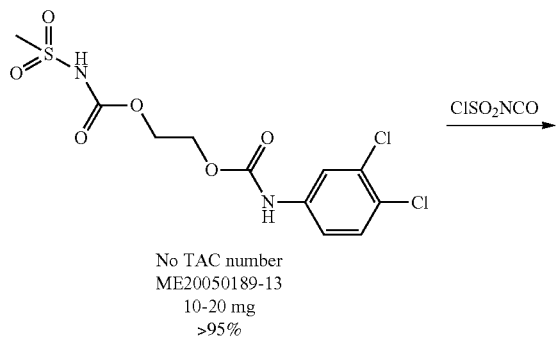

For the synthesis of the next class of compounds according to Synthetic scheme 2 building block 1 was synthesized in low yield 1.27 g (36%), this amount was enough to synthesize enough of the desired end compounds. Also building block 2 was prepared in high yield 456 mg (100%). The first test reaction starting from building block 1 to end product TAC1_011 was successful. After purification by flash chromatography about 50 mg product was isolated. Refluxing building block 2 and isopropylamine in dichloromethane for 2 days gave complete conversion to end product TAC1_012. This batch was purified by flash chromatography and yielded about 50 mg end product.

Two reactions were performed to access the end product TAC1-1009 starting from building block 1, using aqueous ammonia and 7N ammonia in MeOH. According to LCMS/TLC analysis the major compound was building block 1 (73%), also an unknown product (19%) was present.

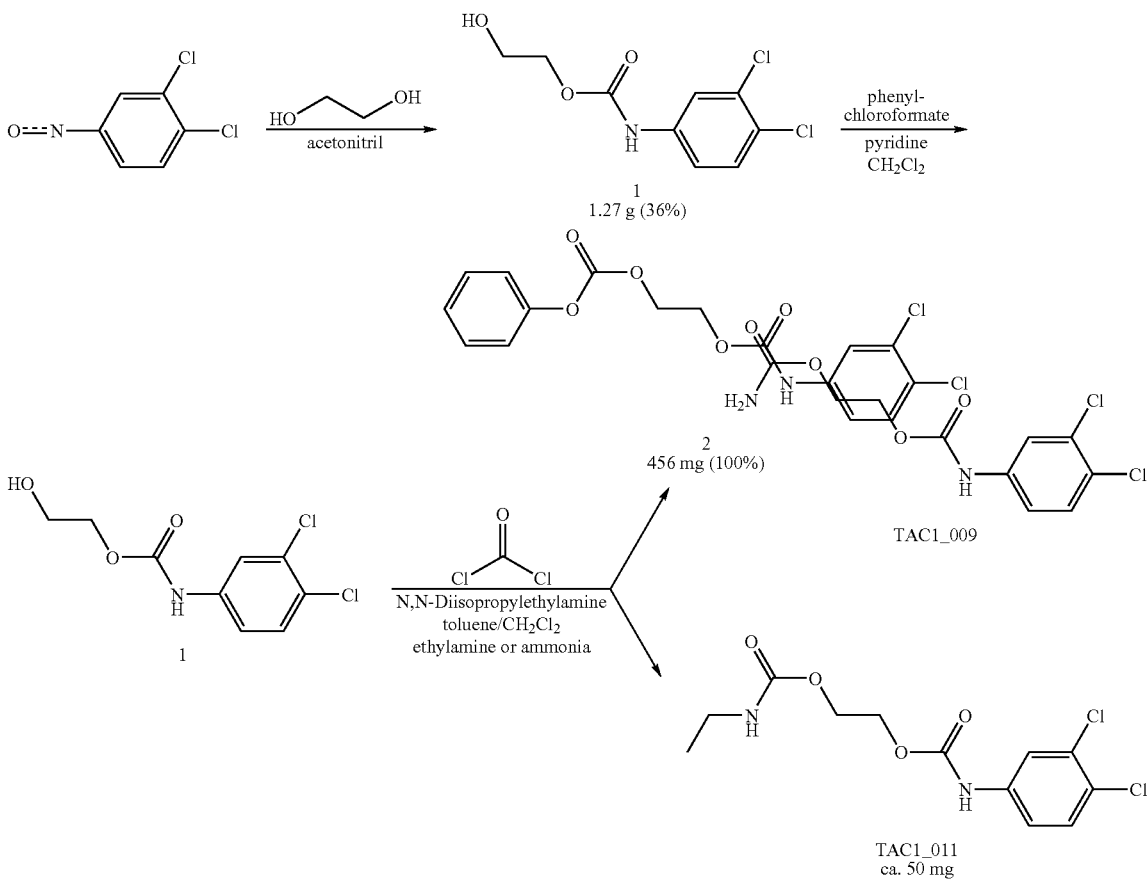

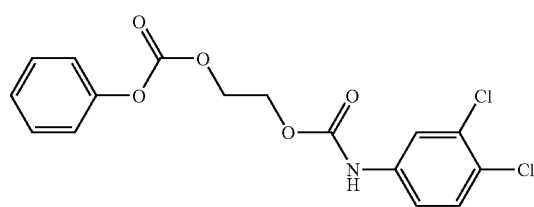
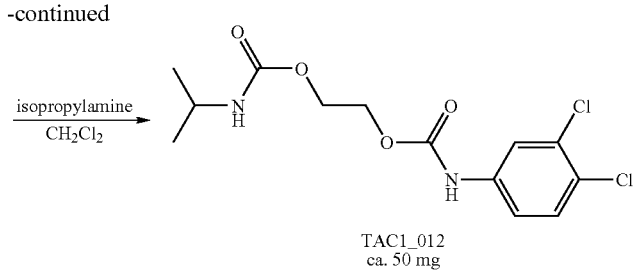

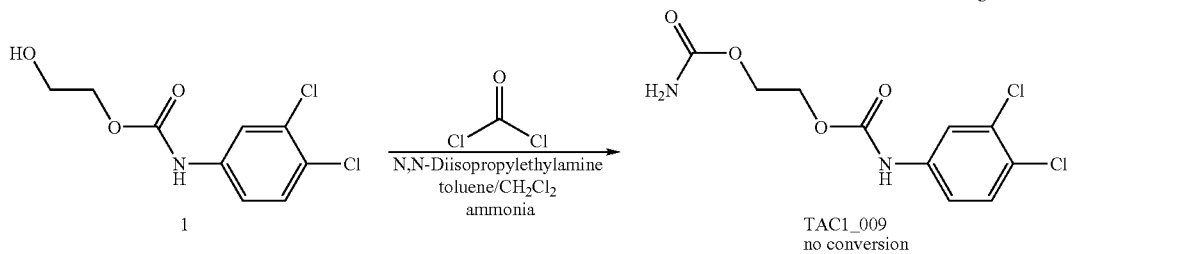

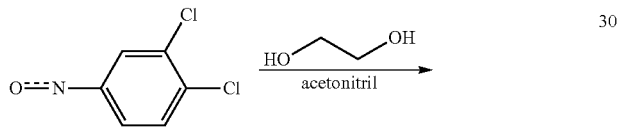

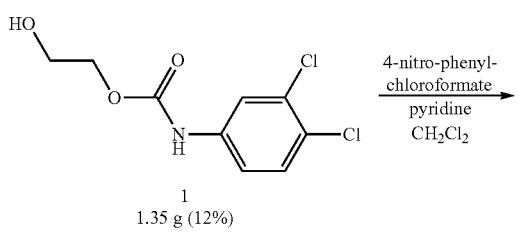

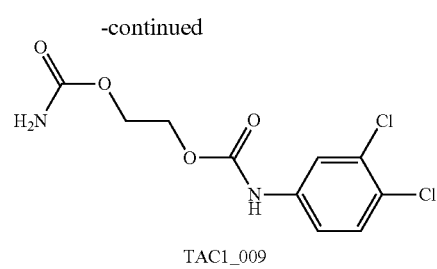

TAC1_009

Resynthesis of alcohol 1 gave 1.35 g (12%) after purification by silica gel column. Some of the alcohol was set in for the coupling with 4-nitro-phenyl-chloroformate to compound 3. The nitro-phenol group is a far better leaving compared to the phenol which we used in an earlier synthesis route. After stirring in a sealed vessel for 2 days at 45° C. using an excess of ammonia, there was no more starting material present. According to LCMS analysis the major product was carbamate TAC1_009.

The reaction of nitro compound 3 with ammonia in MeOH and $CH_2Cl_2$ gave 51 mg of the desired compound TAC1_009. This compound was pure according to $^1$H-NMR but contained some impurities according to LCMS analysis. Purification of the final compound has been done.

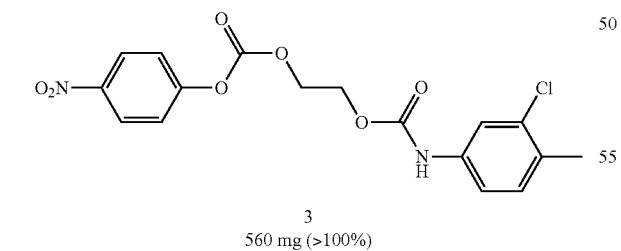

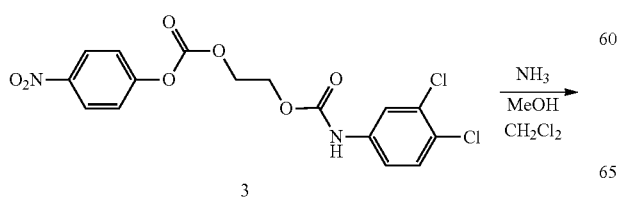

At first there was no conversion to the desired end product TAC1_010. When the reaction was performed in toluene instead of CH$_2$Cl$_2$ there was sufficient conversion to the end product. After purification by flash chromatography about 30 mg of end product TAC1_010 was isolated.

Following Synthetic scheme 3 coupling of N-Boc protected ethanolamine 5 with the isocyanate 4 gave 620 mg (18%) of compound 6 after purification.

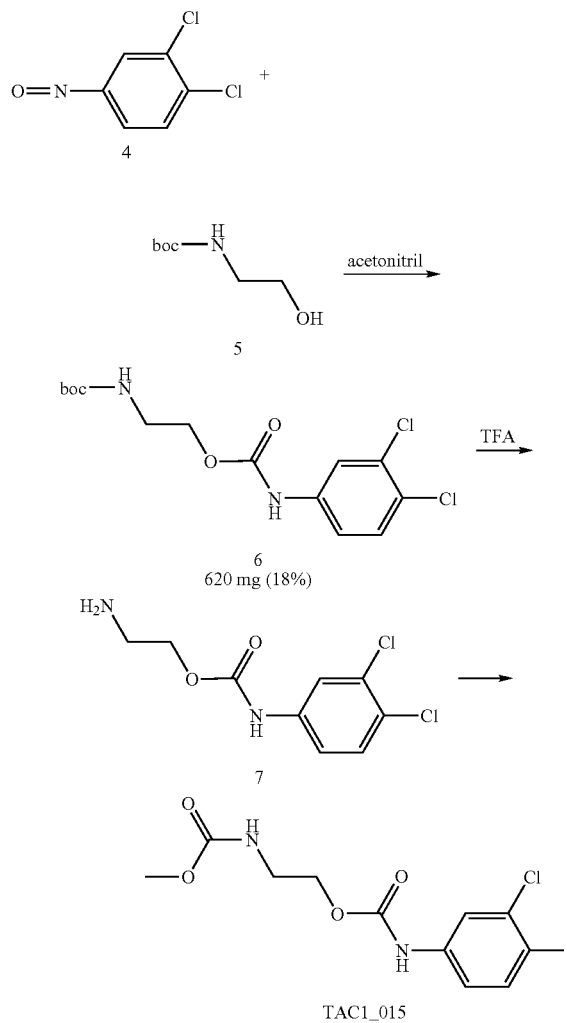

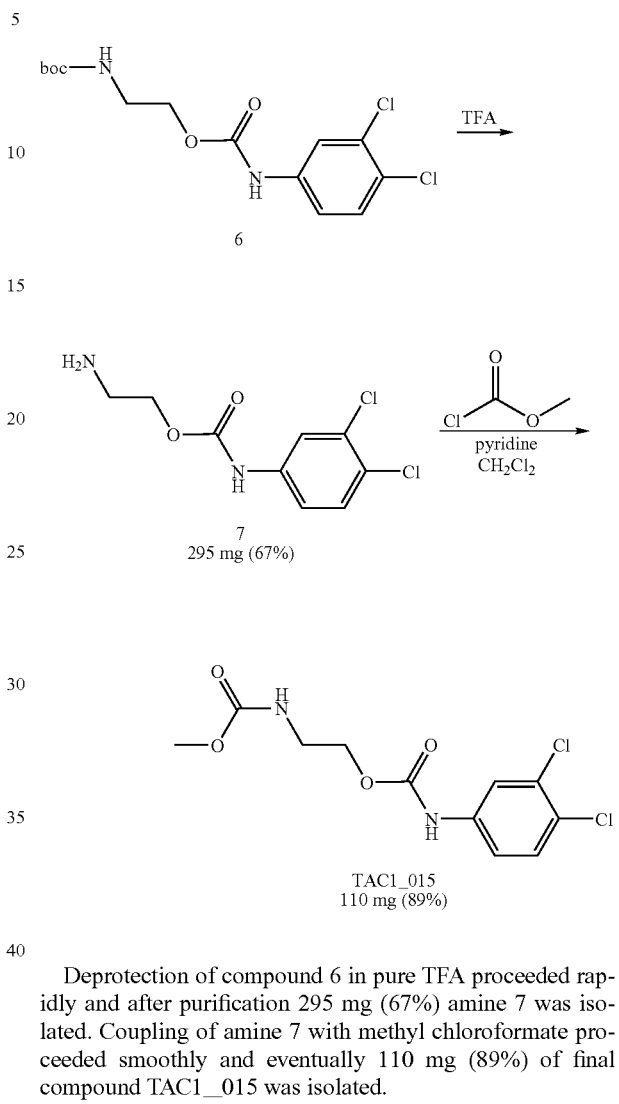

Deprotection of compound 6 in pure TFA proceeded rapidly and after purification 295 mg (67%) amine 7 was isolated. Coupling of amine 7 with methyl chloroformate proceeded smoothly and eventually 110 mg (89%) of final compound TAC1_015 was isolated.

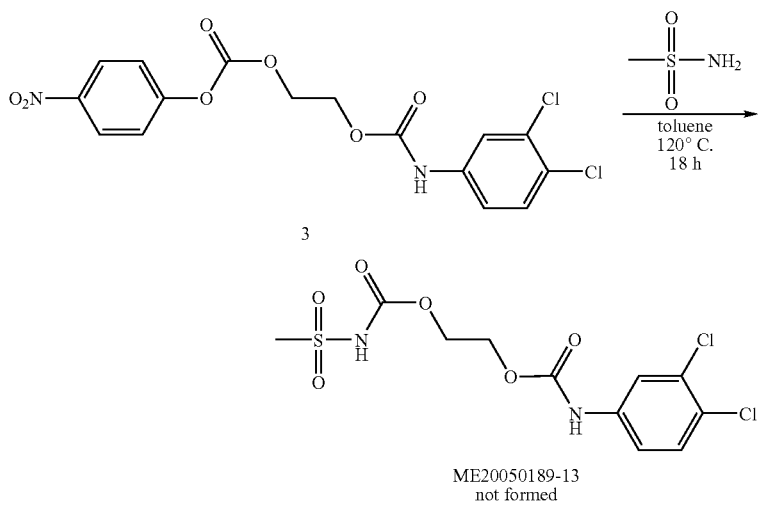

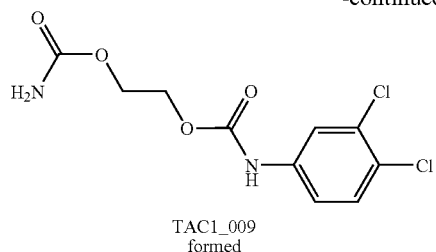

TAC1_009
formed

Nitro compound 3 and an excess of methane sulfonamide (10 equivalents) in toluene were heated to 120° C. in a sealed vessel overnight. According to TLC analysis there was complete conversion to a new product. The aqueous work up involves washing with aqueous saturated sodium bicarbonate and brine. Subsequent purification by flash chromatography gave surprisingly 64 mg carbamate TAC1_009 according to LCMS analysis.

This reaction was repeated and directly purified by flash chromatography. This also gave carbamate TAC1_009 according to LCMS and $^1$H-NMR analysis.

When the reaction was performed in an open glassware setup using 5 equivalents of methane sulfonamide there was no conversion after stirring at 120° C. overnight.

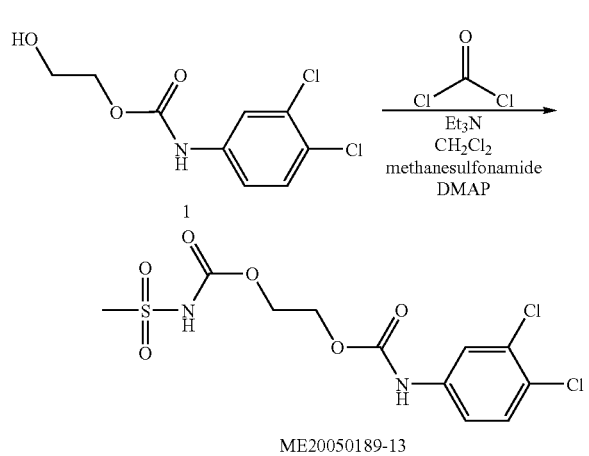

ME20050189-13

Coupling of alcohol 1 with phosgene and subsequently addition of methane sulfonamide gave not the desired compound ME20050189-13. According to LCMS analysis the major product was alcohol 1.

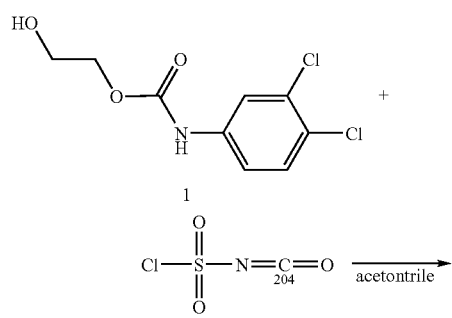

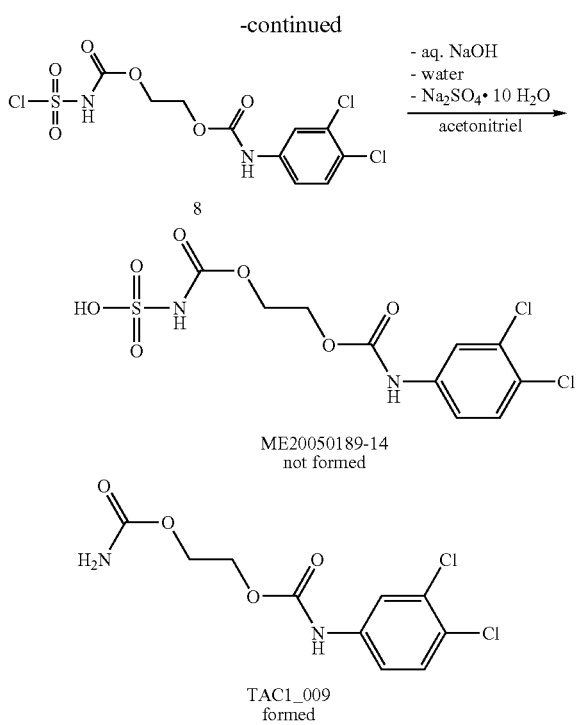

The reaction of alcohol 1 with chlorosulfonyl isocyanate proceeded rapidly to sulfonyl chloride 8. This compound was not isolated but directly set in under three different reaction conditions. Surprisingly only carbamate TAC1_009 was formed in all three cases according to LCMS analysis. In the case were sulfonyl chloride 8 was stirred up with $Na_2SO_4·10H_2O$ (5 equivalents) the reaction mixture was directly purified by flash chromatography. In total 70 mg (60%) of carbamate TAC1_009 was isolated. The structure was confirmed by LCMS and $^1$H-NMR analysis.

Example 4

Further MIC tests, performed as in Example 1, were performed on several of the above synthesized compounds. The results of these tests are summarized in Table 5 below.

TABLE 5

| Antibiotic | | MIC-value (μg/ml) S. aureus ATCC6538 | MIC-value (μg/ml) S. aureus ATCC6538 duplo |
|---|---|---|---|
| TAC 1 (BAS 00674552) | NewCo003 | 25 | 6.25 |

TABLE 5-continued

| Antibiotic | | MIC-value (μg/ml) S. aureus ATCC6538 | MIC-value (μg/ml) S. aureus ATCC6538 duplo |
|---|---|---|---|
| TAC 1_007 | NewCo0015 | 12.5 | 25 |
| TAC 1_005 | NewCo0014 | 100 | 50 |
| TAC 1_009 | NewCo004 | 100 | 50 |
| TAC 1_010 | NewCo008 | 100 | 50 |
| TAC 1_011 | NewCo005 | 100 | 100 |

The invention claimed is:

1. A method of treating infections of Gram-positive bacteria, comprising administering an effective amount of a compound of Formula (I)

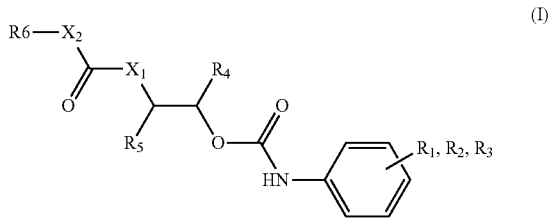

wherein $R_1$, $R_2$, $R_3$ are each independently hydrogen, halogen, loweralkyl, loweralkoxy, substituted loweralkyl or loweralkoxy, $R_4$ and $R_5$ are each independently hydrogen or loweralkyl, $R_6$ is hydrogen, loweralkyl, loweralkoxy, aryl, substituted loweralkyl, loweralkoxy or aryl, $X_1$ is NH or O, $X_2$ is $CH_2$, NH or O, with the proviso that $X_1$ and $X_2$ can not be both NH or both O, or a pharmaceutically acceptable salt or ester thereof.

2. The method of claim 1, wherein the infection is a bacterial infection and the bacterial infection is a *Staphylococcus aureus* infection.

3. The method of claim 1, wherein the compound of Formula (I) is selected from the group consisting of (3,4-dichloro-phenyl)-carbamic acid 2-carbamoyloxy-ethyl ester, (3,4-dichloro-phenyl)-carbamic acid 2-ethylcarbamoyloxy-ethyl ester, (3,4-dichloro-phenyl)-carbamic acid 2-methanesulfonylcarbamoyloxy-ethyl ester, (3,4-dichloro-phenyl)-carbamic acid 2-acetylamino-ethyl ester, (3,4-dichloro-phenyl)-carbamic acid 2-methylcarbamoyloxy-ethyl ester, (3,4-dichloro-phenyl)-carbamic acid 2-isopropylcarbamoyloxy-ethyl ester, (3,4-dichloro-phenyl)-carbamic acid 2-(sulfonic acid)carbamoyloxy-ethyl ester, (3,4-dichloro-phenyl)-carbamic acid 2(2-methoxy-acetylamino)-ethyl ester, (3,4-dichloro-phenyl)-carbamic acid 2-isobutoxycarbonylamino-1-methyl-ethyl ester, (3,4-dimethoxy-phenyl)-carbamic acid 2-isobutoxycarbonylamino-1-methyl-ethyl ester, p-tolyl-carbamic acid 2-isobutoxycarbonylamino-1-methyl-ethyl ester, (4-trifluoromethyl-phenyl)-carbamic acid 2-isobutoxycarbonylamino-1-methyl-ethyl ester, (3,4-difluoro-phenyl)-carbamic acid 2-isobutoxycarbonylamino-1-methyl-ethyl ester, (3,4-bis-trifluoromethyl-phenyl)-carbamic acid 2-isobutoxycarbonylamino-1-methyl-ethyl ester, (4-methoxy-phenyl)-carbamic acid 2-isobutoxycarbonylamino-1-methyl-ethyl ester, and (3-trifluoromethyl-phenyl)-carbamic acid 2-isobutoxycarbonylamino-1-methyl-ethyl ester.

4. The method of claim 1, wherein $R_1$ and $R_2$ are both Cl, and wherein $R_3$ is H, or a pharmaceutically acceptable salt, ester or pro-drug thereof.

5. The method of claim 4, wherein $R_3$=H, $R_4$=H or $CH_3$, $R_5$=H, $CH_3$ or $CH_2CH_3$, $X_1$=NH, $X_2$=O, $R_6$ is $CH_3$, $CH_2CH_3$, $CH(CH_3)_2$ or $CH_2CH(CH_3)_2$, or a pharmaceutically acceptable salt, ester or pro-drug thereof.

6. The method of claim 5, wherein $R_3$=H, $R_4$=$CH_3$, $R_5$=H, $X_1$=NH, $R_6$ is $CH_2CH(CH_3)_2$, or a pharmaceutically acceptable salt, ester or pro-drug thereof.

7. The method of claim 1, wherein the effective amount of the compound of Formula (I) is administered in the form of a pharmaceutical composition comprising a compound according to Formula (I), or a pharmaceutically acceptable carrier.

8. The method of claim 7, wherein the compound of Formula (I) is selected from the group consisting of (3,4-dichloro-phenyl)-carbamic acid 2-carbamoyloxy-ethyl ester, (3,4-dichloro-phenyl)-carbamic acid 2-ethylcarbamoyloxy-ethyl ester, (3,4-dichloro-phenyl)-carbamic acid 2-methanesulfonylcarbamoyloxy-ethyl ester, (3,4-dichloro-phenyl)-carbamic acid 2-acetylamino-ethyl ester, (3,4-dichloro-phenyl)-carbamic acid 2-methylcarbamoyloxy-ethyl ester, (3,4-dichloro-phenyl)-carbamic acid 2-isopropylcarbamoyloxy-ethyl ester, (3,4-dichloro-phenyl)-carbamic acid 2-(sulfonic acid)carbamoyloxy-ethyl ester, (3,4-dichloro-phenyl)-carbamic acid 2(2-methoxy-acetylamino)-ethyl ester, (3,4-dichloro-phenyl)-carbamic acid 2-isobutoxycarbonylamino-1-methyl-ethyl ester, (3,4-dimethoxy-phenyl)-carbamic acid 2-isobutoxycarbonylamino-1-methyl-ethyl ester, p-tolyl-carbamic acid 2-isobutoxycarbonylamino-1-methyl-ethyl ester, (4-trifluoromethyl-phenyl)-carbamic acid 2-isobutoxycarbonylamino-1-methyl-ethyl ester, (3,4-difluoro-phenyl)-carbamic acid 2-isobutoxycarbonylamino-1-methyl-ethyl ester, (3,4-bis-trifluoromethyl-phenyl)-carbamic acid 2-isobutoxycarbonylamino-1-methyl-ethyl ester, (4-methoxy-phenyl)-carbamic acid 2-isobutoxycarbonylamino-1-methyl-ethyl ester, and (3-trifluoromethyl-phenyl)-carbamic acid 2-isobutoxycarbonylamino-1-methyl-ethyl ester.

* * * * *